(12) United States Patent
Andino et al.

(10) Patent No.: US 9,731,097 B2
(45) Date of Patent: Aug. 15, 2017

(54) STABILIZING DEVICE HAVING A LOCKING COLLET

(75) Inventors: Rafael V. Andino, Grayson, GA (US); Christopher J. Brooks, Glen Cove, NY (US)

(73) Assignee: Venetec International, Inc., Murray Hill, NJ (US)

( * ) Notice: Subject to any disclaimer, the term of this patent is extended or adjusted under 35 U.S.C. 154(b) by 1173 days.

(21) Appl. No.: 13/498,121

(22) PCT Filed: Oct. 6, 2010

(86) PCT No.: PCT/US2010/051664
§ 371 (c)(1),
(2), (4) Date: Jul. 3, 2012

(87) PCT Pub. No.: WO2011/044259
PCT Pub. Date: Apr. 14, 2011

(65) Prior Publication Data
US 2012/0265147 A1    Oct. 18, 2012

Related U.S. Application Data

(60) Provisional application No. 61/249,209, filed on Oct. 6, 2009.

(51) Int. Cl.
*A61M 5/32* (2006.01)
*A61M 25/02* (2006.01)

(52) U.S. Cl.
CPC ....... *A61M 25/02* (2013.01); *A61M 2025/024* (2013.01); *A61M 2025/028* (2013.01); *A61M 2025/0266* (2013.01)

(58) Field of Classification Search
CPC ....... A61M 25/02; A61M 25/03; A61M 25/04
USPC ......................................... 604/108, 174–180
See application file for complete search history.

(56) References Cited

U.S. PATENT DOCUMENTS

| | | |
|---|---|---|
| 2,402,306 A | 6/1946 | Turkel |
| 2,525,398 A | 10/1950 | Collins |
| 2,533,961 A | 12/1950 | Rousseau et al. |
| 3,046,984 A | 7/1962 | Eby |
| 3,064,648 A | 11/1962 | Bujan |
| 3,167,072 A | 1/1965 | Stone et al. |
| 3,194,235 A | 7/1965 | Cooke |

(Continued)

FOREIGN PATENT DOCUMENTS

| | | |
|---|---|---|
| CA | 1 311 977 | 12/1992 |
| CA | 1 318 824 | 6/1993 |

(Continued)

OTHER PUBLICATIONS

International Search Report and Written Opinion issued on Jul. 21, 2010 for International Application No. PCT/US2010/035004.

(Continued)

*Primary Examiner* — Phillip Gray
(74) *Attorney, Agent, or Firm* — Rutan & Tucker, LLP

(57) ABSTRACT

A medical article, such as a catheter hub, is stabilized on a patient with a retainer having a base and clamp or moveable collet. A lever is configured to move the collet in a longitudinal direction relative to the based to secure the medical article to the retainer. When rotated, the lever pulls the collet in a direction away from the patient while collapsing the collet around at least a portion of the catheter hub.

20 Claims, 8 Drawing Sheets

(56) References Cited

U.S. PATENT DOCUMENTS

| | | |
|---|---|---|
| 3,245,567 A | 4/1966 | Knight |
| 3,288,137 A | 11/1966 | Lund |
| 3,394,954 A | 7/1968 | Sams |
| 3,493,238 A | 2/1970 | Ludwig |
| 3,529,597 A | 9/1970 | Fuzak |
| 3,589,361 A | 6/1971 | Loper et al. |
| 3,630,195 A | 12/1971 | Santomieri |
| 3,677,250 A | 7/1972 | Thomas |
| 3,686,896 A | 8/1972 | Rutter |
| 3,766,915 A | 10/1973 | Rychlik |
| 3,812,851 A | 5/1974 | Rodriguez |
| 3,817,240 A | 6/1974 | Ayres |
| 3,826,254 A | 7/1974 | Mellor |
| 3,834,380 A | 9/1974 | Boyd |
| 3,856,020 A | 12/1974 | Kovac |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,934,576 A | 1/1976 | Danielsson |
| 3,942,228 A | 3/1976 | Buckman et al. |
| 3,973,565 A | 8/1976 | Steer |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| D252,822 S | 9/1979 | McFarlane |
| 4,170,993 A | 10/1979 | Alvarez |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,250,880 A | 2/1981 | Gordon |
| 4,275,721 A | 6/1981 | Olson |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,516,968 A | 5/1985 | Marshall et al. |
| 4,517,971 A | 5/1985 | Sorbonne |
| 4,561,857 A | 12/1985 | Sacks |
| 4,563,177 A | 1/1986 | Kamen |
| 4,585,435 A | 4/1986 | Vaillancourt |
| 4,585,444 A | 4/1986 | Harris |
| 4,631,056 A | 12/1986 | Dye |
| 4,632,670 A | 12/1986 | Muller |
| 4,633,863 A | 1/1987 | Filips et al. |
| 4,645,492 A | 2/1987 | Weeks |
| 4,650,473 A | 3/1987 | Bartholomew et al. |
| 4,660,555 A | 4/1987 | Payton |
| 4,666,434 A | 5/1987 | Kaufman |
| 4,669,458 A | 6/1987 | Abraham et al. |
| 4,693,710 A | 9/1987 | McCool |
| 4,711,636 A | 12/1987 | Bierman |
| 4,723,948 A | 2/1988 | Clark et al. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,792,163 A | 12/1988 | Kulle |
| 4,795,429 A | 1/1989 | Feldstein |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,895,570 A * | 1/1990 | Larkin ............ A61M 39/1011 604/411 |
| 4,897,082 A | 1/1990 | Erskine |
| 4,898,587 A | 2/1990 | Mera |
| 4,919,654 A | 4/1990 | Kalt |
| 4,934,375 A | 6/1990 | Cole et al. |
| 4,941,882 A | 7/1990 | Ward et al. |
| 4,955,864 A | 9/1990 | Hajduch |
| 4,966,582 A | 10/1990 | Sit et al. |
| 4,976,698 A | 12/1990 | Stokley |
| 4,976,700 A | 12/1990 | Tollini |
| 4,981,469 A | 1/1991 | Whitehouse et al. |
| 4,981,475 A | 1/1991 | Haindl |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| 5,074,847 A | 12/1991 | Greenwell et al. |
| D323,390 S | 1/1992 | Paine et al. |
| 5,084,026 A | 1/1992 | Shapiro |
| 5,098,048 A | 3/1992 | Chen |
| 5,105,807 A | 4/1992 | Kahn et al. |
| 5,112,313 A | 5/1992 | Sallee |
| 5,116,324 A | 5/1992 | Brierley et al. |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,163,913 A | 11/1992 | Rantanen-Lee et al. |
| 5,167,630 A | 12/1992 | Paul |
| 5,192,273 A | 3/1993 | Bierman |
| 5,192,274 A | 3/1993 | Bierman |
| 5,195,981 A | 3/1993 | Johnson |
| 5,215,532 A | 6/1993 | Atkinson |
| 5,238,010 A | 8/1993 | Grabenkort |
| 5,248,306 A | 9/1993 | Clark et al. |
| 5,263,943 A | 11/1993 | Vanderbrook |
| 5,267,967 A | 12/1993 | Schneider |
| 5,290,248 A | 3/1994 | Bierman et al. |
| 5,306,253 A | 4/1994 | Brimhall |
| 5,306,256 A | 4/1994 | Jose |
| D347,060 S | 5/1994 | Bierman |
| 5,314,411 A | 5/1994 | Bierman et al. |
| 5,328,487 A | 7/1994 | Starchevich |
| 5,330,438 A | 7/1994 | Gollobin et al. |
| 5,336,195 A | 8/1994 | Daneshvar |
| 5,341,411 A | 8/1994 | Hashimoto |
| 5,344,414 A | 9/1994 | Lopez et al. |
| 5,354,282 A * | 10/1994 | Bierman ............ A61M 5/32 604/174 |
| 5,356,379 A | 10/1994 | Vaillancourt |

(56) References Cited

U.S. PATENT DOCUMENTS

| | | |
|---|---|---|
| 5,356,391 A | 10/1994 | Stewart |
| 5,370,627 A | 12/1994 | Conway |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,395,344 A | 3/1995 | Beisang et al. |
| 5,413,120 A | 5/1995 | Grant |
| 5,413,562 A | 5/1995 | Swauger |
| D359,120 S | 6/1995 | Sallee et al. |
| 5,456,671 A | 10/1995 | Bierman |
| 5,470,321 A | 11/1995 | Forster et al. |
| D364,922 S | 12/1995 | Bierman |
| 5,484,425 A | 1/1996 | Fischell et al. |
| 5,496,283 A | 3/1996 | Alexander |
| 5,507,535 A | 4/1996 | McKamey et al. |
| 5,531,695 A | 7/1996 | Swisher |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| D377,831 S | 2/1997 | Bierman |
| 5,605,546 A | 2/1997 | Wolzinger et al. |
| 5,620,427 A | 4/1997 | Werschmidt et al. |
| 5,626,565 A | 5/1997 | Landis et al. |
| 5,643,217 A | 7/1997 | Dobkin |
| 5,664,581 A | 9/1997 | Ashley |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,690,617 A | 11/1997 | Wright |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,755,225 A | 5/1998 | Hutson |
| 5,800,402 A | 9/1998 | Bierman |
| 5,800,410 A | 9/1998 | Gawreluk |
| 5,810,781 A | 9/1998 | Bierman |
| 5,814,021 A | 9/1998 | Balbierz |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,251 A | 3/1999 | Luther |
| 5,885,254 A | 3/1999 | Matyas |
| 5,897,519 A | 4/1999 | Shesol et al. |
| 5,947,931 A | 9/1999 | Bierman |
| 6,050,934 A | 4/2000 | Mikhail et al. |
| D425,619 S | 5/2000 | Bierman |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,139,532 A | 10/2000 | Howell et al. |
| D433,503 S | 11/2000 | Powers et al. |
| 6,213,979 B1 | 4/2001 | Bierman |
| 6,213,996 B1 | 4/2001 | Jepson et al. |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,258,066 B1 | 7/2001 | Urich |
| 6,270,086 B1 | 8/2001 | Lloyd |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 | 8/2002 | Bierman et al. |
| 6,428,516 B1 | 8/2002 | Bierman et al. |
| 6,436,073 B1 | 8/2002 | Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,517,522 B1 | 2/2003 | Bell |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell |
| 6,626,890 B2 | 9/2003 | Nguyen et al. |
| 6,652,487 B1 | 11/2003 | Cook |
| 6,663,600 B2 | 12/2003 | Bierman et al. |
| 6,673,046 B2 | 1/2004 | Bierman et al. |
| 6,689,104 B2 | 2/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,824,527 B2 | 11/2004 | Gollobin |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman |
| 7,070,580 B2 | 7/2006 | Nielsen |
| 7,090,660 B2 | 8/2006 | Roberts et al. |
| D528,206 S | 9/2006 | Bierman |
| 7,144,387 B2 | 12/2006 | Millerd |
| 7,153,291 B2 | 12/2006 | Bierman |
| 7,354,421 B2 | 4/2008 | Bierman |
| 7,491,190 B2 | 2/2009 | Bierman |
| 7,935,083 B2 | 5/2011 | Bierman et al. |
| 2002/0068904 A1 | 6/2002 | Bierman et al. |
| 2002/0099360 A1 | 7/2002 | Bierman |
| 2002/0133121 A1 | 9/2002 | Bierman |
| 2003/0055382 A1 | 3/2003 | Schaeffer |
| 2003/0163096 A1 | 8/2003 | Swenson et al. |
| 2003/0181870 A1 | 9/2003 | Bressler et al. |
| 2003/0229313 A1 | 12/2003 | Bierman |
| 2004/0102736 A1 | 5/2004 | Bierman |
| 2004/0111067 A1 | 6/2004 | Kirchhofer |
| 2004/0204685 A1 | 10/2004 | Wright et al. |
| 2005/0096606 A1 | 5/2005 | Millerd |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0079740 A1 | 4/2006 | Silver et al. |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270994 A1 | 11/2006 | Bierman |
| 2006/0270995 A1 | 11/2006 | Bierman |
| 2007/0016166 A1* | 1/2007 | Thistle ............... A61M 39/0208 604/533 |
| 2007/0016167 A1 | 1/2007 | Smith et al. |
| 2007/0250021 A1 | 10/2007 | Brimhall et al. |
| 2008/0045905 A1 | 2/2008 | Chawki |
| 2008/0300543 A1 | 12/2008 | Abriles et al. |

(56) References Cited

U.S. PATENT DOCUMENTS

| | | |
|---|---|---|
| 2010/0049139 A1 | 2/2010 | Kiyono et al. |
| 2010/0298777 A1 | 11/2010 | Nishtala |

FOREIGN PATENT DOCUMENTS

| | | |
|---|---|---|
| CA | 2690234 A1 | 12/2008 |
| DE | 2341297 A1 | 4/1975 |
| EP | 0114677 A2 | 8/1984 |
| EP | 0169704 A1 | 1/1986 |
| EP | 0247590 A2 | 12/1987 |
| EP | 0263789 A1 | 4/1988 |
| EP | 0367549 A2 | 5/1990 |
| EP | 0720836 A2 | 7/1996 |
| EP | 0356683 | 3/2000 |
| FR | 2 922 458 A1 | 4/2009 |
| GB | 2063679 A | 6/1981 |
| GB | 2086466 A | 5/1982 |
| GB | 2178811 A | 2/1987 |
| WO | 9005559 A1 | 5/1990 |
| WO | WO 94/21319 | 9/1994 |
| WO | WO 97/15337 | 5/1997 |
| WO | WO 99/55409 | 11/1999 |
| WO | 2004016309 A2 | 2/2004 |
| WO | WO 2009/032008 | 3/2009 |
| WO | WO 2010/132837 | 11/2010 |

OTHER PUBLICATIONS

CA 2775571 filed Mar. 27, 2012 Office Action dated Aug. 8, 2016.
U.S. Appl. No. 13/577,425, filed Sep. 17, 2012, Non-Final Office Action of dated Oct. 17, 2016.
AU 2010303477 filed Oct. 6, 2010 Examiner's Search Report dated Oct. 22, 2015.
Cravens, et al. "Urinary Catheter Management" American Family Physician, vol. 61, No. 2, pp. MDG 000273-MDG 000282, dated Jan. 15, 2000.
Dale® Foley Catheter Holder brochure, pp. MDG 000344-MDG 000346, 2002.
Expert Discusses Strategies to Prevent CAUTIs, Infection Control Today, pp. MDG 000603-MDG-000609, Jun. 2005.
Grip-Lok Universal Tubing Securement brochure, pp. MDG 000364-MDG 000366, 2005-2006.
Grip-Lok™ Universal Tubing Securement brochure, pp. MDG 000348-MDG 000349, Jun. 12, 2012.
M.C. Johnson Co., Gath-Secure®—http://www.mcjohnson.com/cath-secure.html, last accessed Jun. 12, 2012.
PCT/US2007/077302 filed Aug. 30, 2007 International Search Report dated Mar. 28, 2008.
PCT/US2010/035004 filed May 14, 2010 International Search Report and Written Opinion dated Jul. 21, 2010.
PCT/US2010/051664 filed Oct. 6, 2010 International Search Report and Written Opinion dated Dec. 2, 2010.
PCT/US2011/026897 filed Mar. 2, 2011 International Search Report dated Apr. 26, 2011.
U.S. Appl. No. 13/320,381, filed Feb. 27, 2012 Final Office Action dated Dec. 17, 2015.
U.S. Appl. No. 13/320,381, filed Feb. 27, 2012 Non-Final Office Action dated Aug. 26, 2015.
U.S. Appl. No. 13/320,381, filed Feb. 27, 2012 Non-Final Office Action dated Jul. 29, 2016.
U.S. Appl. No. 13/415,644, filed Aug. 3, 2012, Advisory Action dated Sep. 24, 2015.
U.S. Appl. No. 13/415,644, filed Aug. 3, 2012, Examiner's Answer dated Jun. 15, 2016.
U.S. Appl. No. 13/415,644, filed Aug. 3, 2012, Non Final Office Action dated Jun. 29, 2015.
U.S. Appl. No. 13/577,425, filed Sep. 17, 2012, Advisory Action of dated Dec. 4, 2015.
U.S. Appl. No. 13/577,425, filed Sep. 17, 2012, Final Office Action of dated Sep. 8, 2015.
U.S. Appl. No. 13/577,425, filed Sep. 17, 2012, Non-Final Office Action of dated May 21, 2015.
U.S. Pat. No. 5,827,230 National Patent Services, Search Report re Patent Validity Study pp. MDG 001319-MDG 001320, dated May 23, 2006.

\* cited by examiner ion as expressed by the claims which follow, its more prominent features will now be discussed briefly. After considering this discussion, and particularly after reading the section entitled "Detailed Description of Certain Embodiments," one will understand how the features of this invention provide several advantages over other securement devices.

STABILIZING DEVICE HAVING A LOCKING COLLET

CROSS-REFERENCE TO RELATED APPLICATIONS

This application is the National Stage of International Application No. PCT/US2010/051664, filed on Oct. 6, 2010, entitled "STABILIZING DEVICE HAVING A LOCKING COLLET," which claims priority under 35 U.S.C. §119(e) to U.S. Provisional Application No. 61/249,209, filed Oct. 6, 2009, entitled "STABILIZING DEVICE HAVING A LOCKING COLLET," both of which are hereby incorporated by reference in their entirety.

BACKGROUND

Field of the Invention

This invention relates to a securement device for use with medical articles. More specifically, this invention relates to an anchoring system which releasably retains a fitting or adaptor of the medical article in position upon a patient.

Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line may be secured to the patient in a variety of ways. Most commonly, this involves taping the catheter or medical line to the patient.

Securing a catheter with tape upon the patient traditionally has certain drawbacks. The use of tape at the insertion site may retain dirt or other contaminant particles, potentially leading to infection of the patient. Additionally, removal of taped dressings may itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line may additionally lead to the build up of adhesive residue on the outer surface of the catheter or medical line. This residue can result in contaminants adhering to the catheter itself, increasing the likelihood of infection of the insertion site. This residue may also make the catheter or medical line stickier and more difficult to handle for medical attendants.

For these reasons, a need exists for an improved way to secure catheters and medical lines to patients where the catheter may remain in place over an extended period of time and may be easily released from the securement device.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide several advantages over other securement devices.

One aspect of the present invention is a securement device for securing a medical article to a patient. The device includes an anchor pad having a lower surface. At least a portion of the lower surface is covered by an adhesive. The device further includes a collet supported by the anchor pad. The collet is movable between an open position and a closed position. The collet exerts a clamping force on the medical article when in the closed position.

Another aspect of the present invention is a securement device for a medical article having a first lumen extending therethrough. The device includes an anchor pad. At least a portion of a lower surface of the anchor pad is covered by an adhesive. The device further includes a base member supported by the anchor pad and forming a second lumen therethrough. The device further includes a member movable relative to the base member between an open position and a closed position. The member and base member define a receptacle for receiving at least a portion of the medical article when in the open position. The device further includes a lever moving the member from the open position to the closed position so as to secure the received portion of the medical article relative to the base member and form a flow passage between the first and second lumens.

Another aspect of the present invention is a retainer for a medical article having a first lumen extending therethrough. The retainer includes a base member forming a second lumen therethrough. The retainer further includes a member movable relative to the base member between an open position and a closed position. The member and base member define a receptacle for receiving at least a portion of the medical article when in the open position. The retainer further includes a lever for moving the member from the open position to the closed position so as to secure the received portion of the medical article relative to the base member.

BRIEF DESCRIPTION OF THE DRAWINGS

The above mentioned and other features of the invention will now be described with reference to the drawings of several embodiments of the present securement device. The illustrated embodiments of the securement device are intended to illustrate, but not to limit the invention. The drawings contain the following figures.

DETAILED DESCRIPTION OF CERTAIN EMBODIMENTS

The following description and Figures describing various preferred embodiments are made to demonstrate various configurations of possible systems in accordance with the current invention. The embodiments illustrated are shown in use with an exemplary connector fitting in the form of a catheter hub. The principles of the present invention, however, are not limited to catheter hubs such as those shown. It will be understood by those of skill in the art in view of the present disclosure that the securement device described can be used with other types of medical articles, including, but not limited to catheters of various design, either with or without connectors, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can be a single medical article or a combination of medical articles.

In addition, various systems will be described in the context of an exemplary securement device incorporating the described systems and techniques. Those of skill in the art will recognize that the techniques described are neither limited to any particular type of securement device, nor to the securement of any particular type of medical article for every described aspect herein.

Figure 1:
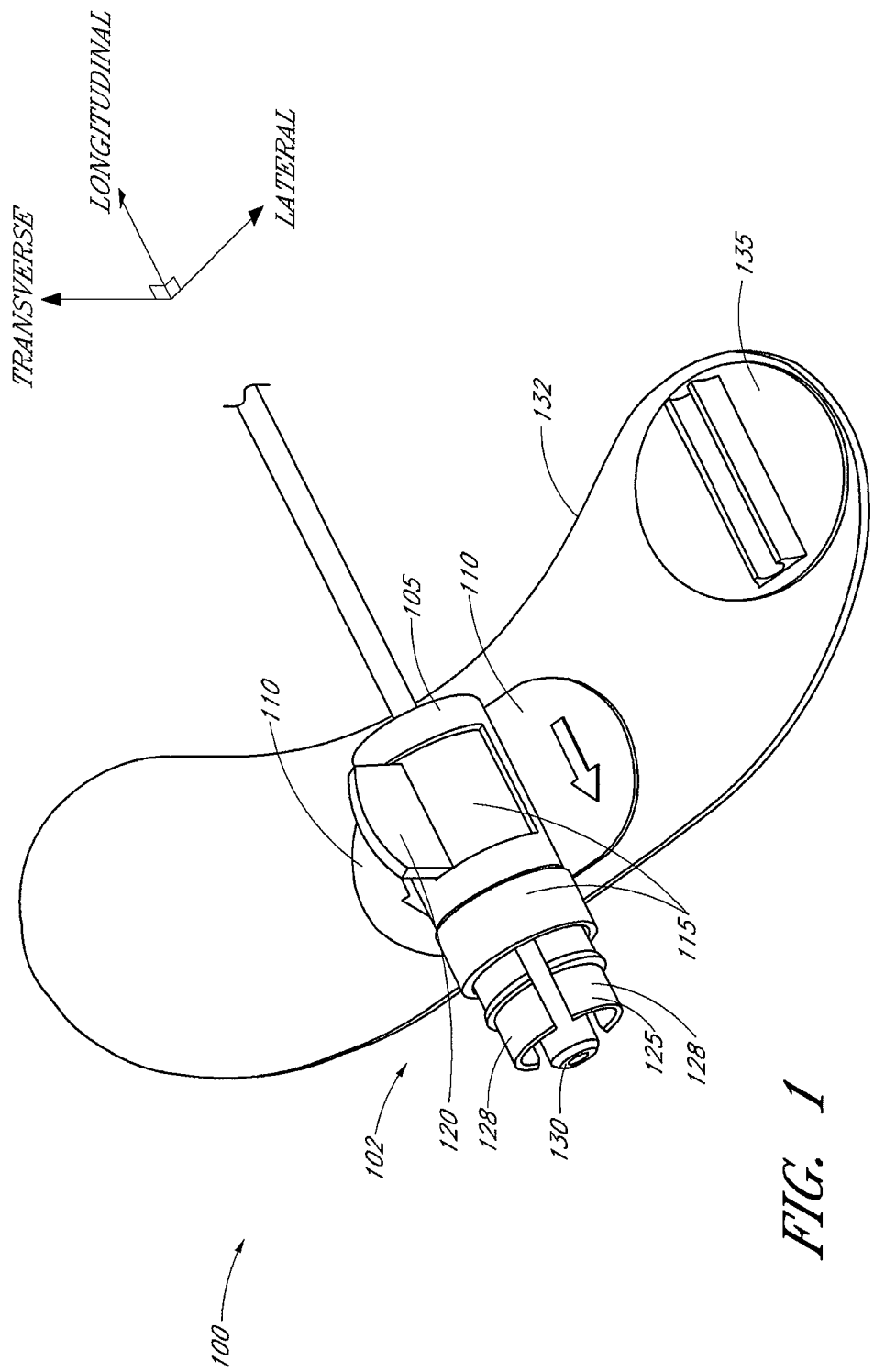
FIG. 1 is a perspective view of a securement device in accordance with a preferred embodiment of the present invention.
Figure 2:
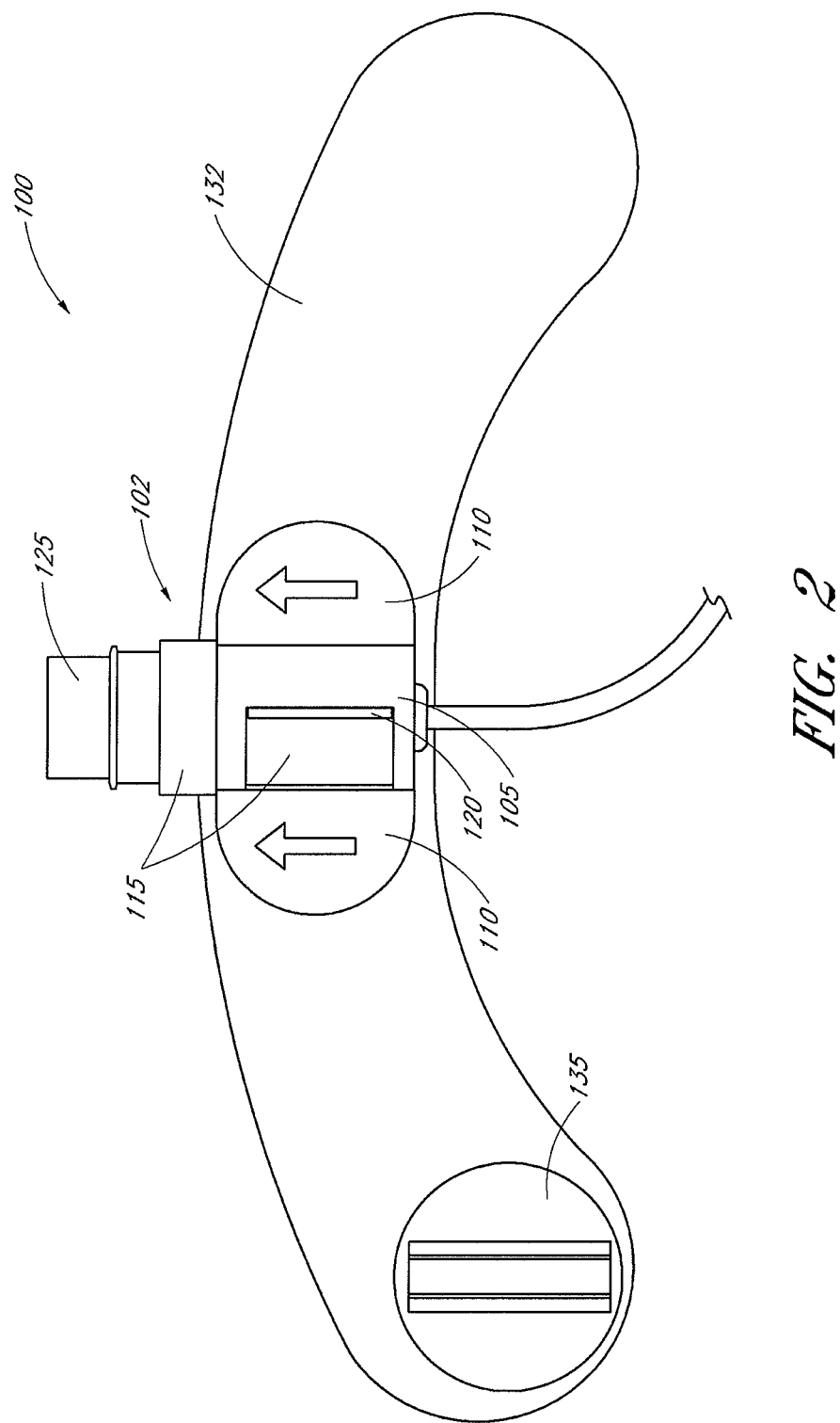
FIG. 2 is a top view of the securement device of FIG. 1 including an anchor pad and retainer.
Figure 3:
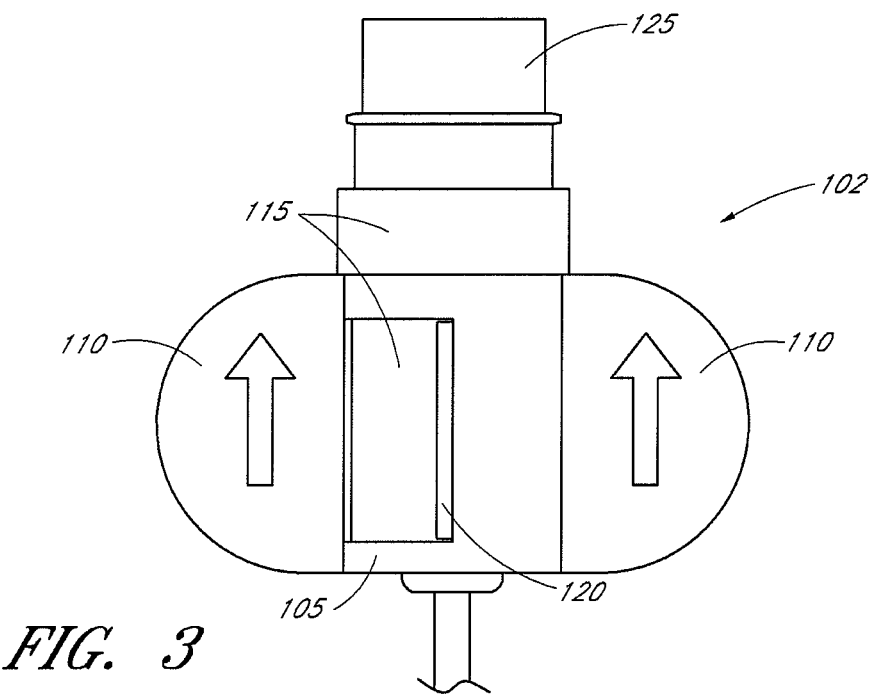
FIG. 3 is top view of the retainer from FIG. 1.
Figure 4:
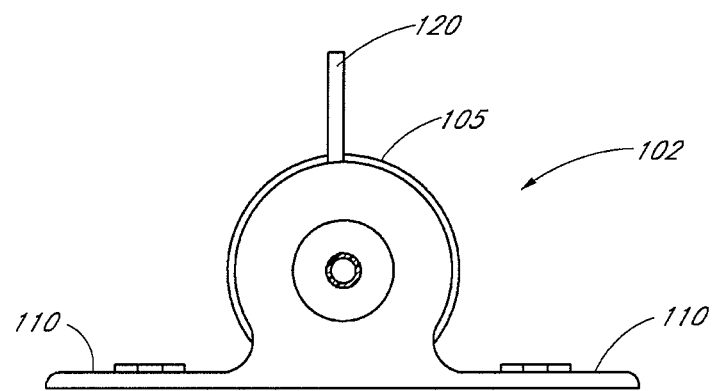
FIG. 4 is a back view of the retainer from FIG. 3.
Figure 5:
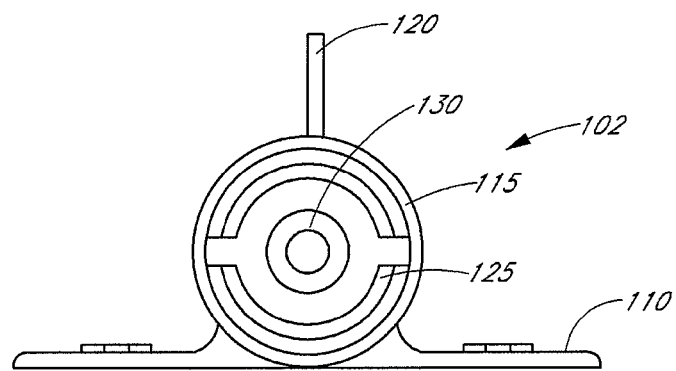
FIG. 5 is a front view of the retainer from FIG. 3.

To assist in the description of the components of the securement device 100, and with respect to the present figures the following coordinate terms are used. A "longitudinal axis" is generally parallel to the central axis extending through the retainer 102, as depicted in FIG. 1. A "lateral axis" is normal to the longitudinal axis and is generally parallel to the plane of the anchor pad 132. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present securement device, are used consistently with the description of the exemplary applications (i.e., the illustrative examples of the use applications). Thus, proximal and distal are used in reference to the center of the patient's body. Also, the terms "top", "bottom", "upper", and "lower" are used in the context of the orientation of the securement, and are not intended to imply a limitation to the orientation that the securement device 100 can assume on the patient.

The securement device 100 secures a medical article, for example, a catheter hub 200, relative to a patient. As shown in FIG. 1-5, the securement device 100 comprises a retainer 102 that is supported by an anchor pad 132. The anchor pad 132 is secured to the skin of the patient, generally by an adhesive disposed upon the bottom or lower surface of the anchor pad 132.

Embodiments of the retainer 102 comprise a clamp 125 for releasably securing a medical article to the retainer 102. The retainer 102 may further include a base 105 and a locking mechanism 115. The base 105 supports the clamp 125 and is secured relative to the anchor pad 132. The locking mechanism 115 actuates the clamp 125 thereby securing the medical article to the retainer 102.

In the illustrated embodiment of FIG. 1, the clamp 125 is arranged so that the clamp 125 receives the medical article by moving the medical article distally along the longitudinal axis towards the clamp 125. Of course the clamp 125 need not be arranged in this way and could alternatively be disposed relative to the retainer 102 so as to receive medical articles moving along, for example, the transverse or lateral axes.

While a single clamp 125 is illustrated in FIG. 1, the retainer 102 may include a plurality of clamps 125 facing in different directions. For example, the retainer 102 can include a first clamp 125 disposed on the proximal end of the retainer 102 and a second clamp 125 disposed on the distal end of the retainer 102. While not illustrated, the second clamp 125 could attach to the distal end of the retainer 102 instead of the illustrated medical line. Another embodiment of the retainer 102 includes a first clamp 125 disposed on the proximal end of the retainer 102 and a second clamp 125 disposed on a side of the retainer 102 so as to receive medical articles moving in a lateral direction. Such a retainer 102 would have a t-shape. For embodiments of the securement device 100 that include the illustrated medical line, the medical line can be integral to the retainer 102 or releasably secured to the retainer 102, via, for example, a luer lock, a luer slip, or another clamp 125.

In the illustrated embodiment, the retainer 102 receives a medical article in the longitudinal direction and secures it in position. The releasable engagement of a medical article is achieved, at least in part, by cooperation between at least a portion of the medical article and the clamp 125. The locking mechanism 115 actuates the clamp 125 which moves at least a portion of the clamp 125 between open and closed positions to release and secure the medical article.

Figure 8:
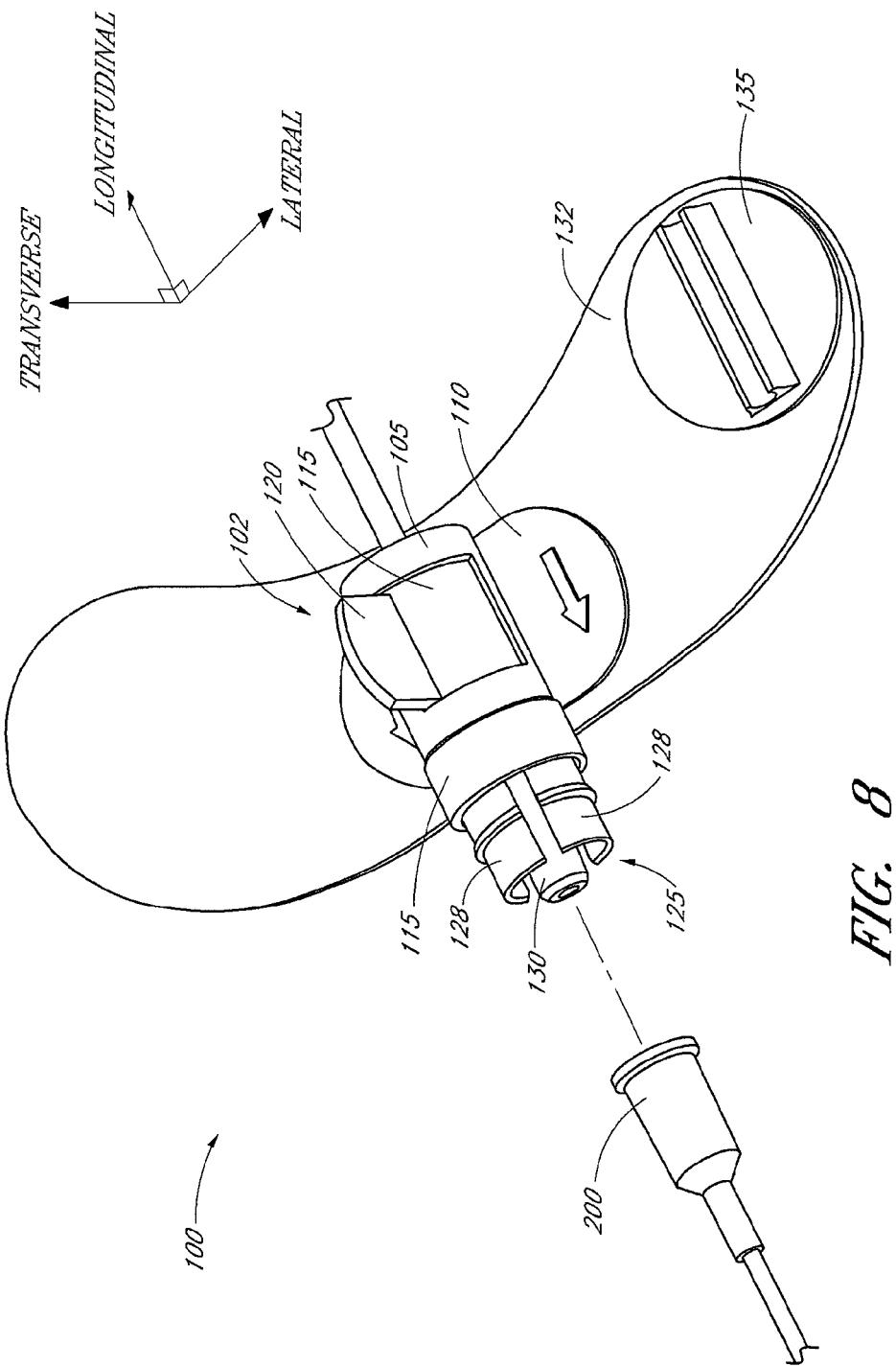
FIG. 8 is a perspective view of the securement device of FIG. 1 in an open condition and aligned with a medical article.

A medical article, for instance an exemplary catheter hub 200 shown in FIG. 8, can be held in position by the retainer 102. The base 105 may comprise a body which receives at least a portion of the clamp 125. For example, the body may have a cylindrical shape which defines a channel. The channel may extend along the longitudinal axis and receive a tubular portion of the clamp 125.

The base 105 is secured to the anchor pad 132. The base 105 may include one or more tabs 110 for this purpose. The tabs 110 increase the size of the contact area between the anchor pad 132 and the base 105 to limit movement of the retainer 102 relative to the anchor pad 132. The tabs 110 extend from the base 105 in the lateral direction. The tabs may be located at the bottom of the base 105 and extend from the base 105 in both lateral directions. The base 105 may further comprise a tubular portion 130 defining a lumen. The lumen is employed to flow liquids and medication to the patient when the medical article is secured to the clamp 125. The tubular portion 130 may be positioned coaxially in the channel of the base 105 and extend in the longitudinal direction.

At least a portion of the locking mechanism 115 may be disposed within the channel of the base 105. The outer surface of the locking mechanism 115 may comprise a generally cylindrical shape that corresponds to a generally cylindrical shape of the channel of the base 105. At least a portion of the locking mechanism 115 may be rotatably coupled to the base 105. The locking mechanism 115 may comprise an actuator or lever 120. Actuation of the lever 120 moves the clamp 125 between the open and closed positions. The lever 120 may be used to rotate the locking mechanism 115 within the channel of the base 105.

The lever 120 is accessible by the healthcare provider. For example, the lever 120 may extend from the outer surface of the locking mechanism 115 and through an opening in the base 105 to allow the healthcare provider to rotate the lever 120. The base 105 may comprise an opening into the cylindrical body of the base 105 for this purpose. The lever 120 may extend through the opening and may be used to rotate the locking mechanism 115 with respect to the base 105.

The locking mechanism 115 may comprise a channel or receiving sleeve for receiving a portion of the clamp 125. A portion of the channel of the locking mechanism 115 may have a decreasing cross-sectional area to form a taper. As the lever 120 of the locking mechanism is rotated about the longitudinal axis, the clamp 125 moves within the channel or receiving sleeve of the locking mechanism 115 in the distal direction. The decreasing cross-sectional area of the sleeve or channel of the locking mechanism 115 gradually closes the clamp 125 about the medical article as the clamp 125 moves in the distal direction relative to the base 105.

For example, the diameter of the channel can have a generally conical shape that decreases in diameter in the longitudinal direction starting from the proximal side of the base 105 near the insertion point of the catheter hub 200. The rate at which the diameter of the channel decreases can vary along the length of the channel. Further the channel may include steps and or grooves which receive corresponding ridges on the clamp 125 to bias the clamp 125 to stay in a specific longitudinal position. For example, a step and corresponding ridge could be disposed along the locking mechanism 115 and clamp 125 so that the step engages the ridge when the clamp 125 is disposed in the closed position.

In certain embodiments the clamp 125 is disposed within the conical channel or sleeve of the locking mechanism 115. The clamp 125 may comprise a collet. The collet forms a collar around the medical article to be secured and exerts a clamping force on the medical article when the collet is tightened via the tapered channel of the locking mechanism 115.

Figure 6:
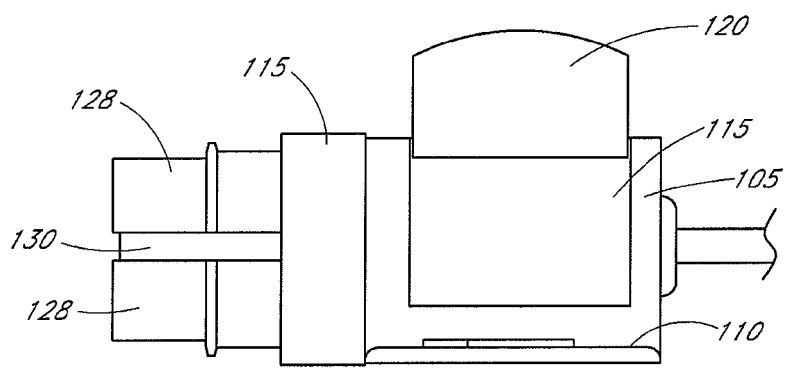
FIG. 6 is a side view of the retainer from FIG. 3 in an open condition.
Figure 7:
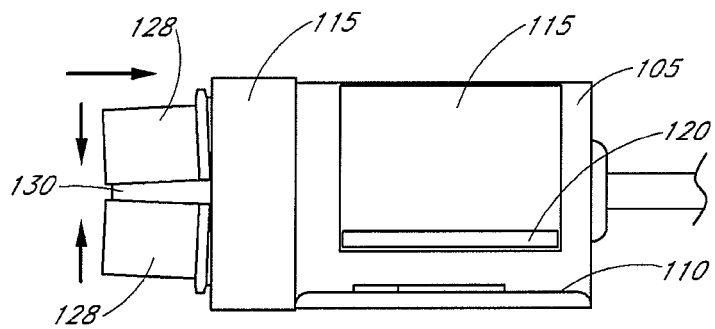
FIG. 7 is a side view of the retainer from FIG. 3 in a closed condition.

The clamp 125 may comprise a body with a plurality of latching members or fingers 128 that are moveable with respect to each other. The latching members 128 may be shaped to form a generally cylindrical shape. The latching members 128 may be configured to receive a portion of the catheter hub 200 when in an open position as shown in FIG. 6. The latching members 128 may further be configured to close around the hub 200 and secure the hub 200 when in a closed position as shown in FIG. 7.

The clamp 125 may be configured to cooperate with locking mechanism 115 to move between an open position and a closed position. For example, the locking mechanism 115 may be configured to open and close the clamp 125. The locking mechanism 115 may be rotatably connected to the clamp 125. Further, the clamp 125 may be configured to move longitudinally within the channel of the locking mechanism 115. Drawing the clamp 125 in the longitudinal direction into the locking mechanism 115 may cause the latching members 128 to move into the closed position as shown in FIG. 7 as the locking mechanism 115 applies an inward force on the latching members 128. As the clamp 125 is moved in the opposite direction longitudinally, the latching members 128 open into the open position as shown in FIG. 6.

Rotation of the locking mechanism 115 between an open position and a closed position may move the clamp 125 between the open position and the closed position. For example, the locking mechanism 115 may comprise a groove along the inner surface of its body, through which the channel extends. The groove may cooperate with the surface of the clamp 125 so that a portion of the clamp 125 is configured to sit in the groove. As the locking mechanism 115 rotates, the clamp 125 moves along the groove. This movement causes the clamp 125 to move in and out of the locking mechanism. Accordingly, the clamp 125 moves between open and closed positions.

Figure 9:
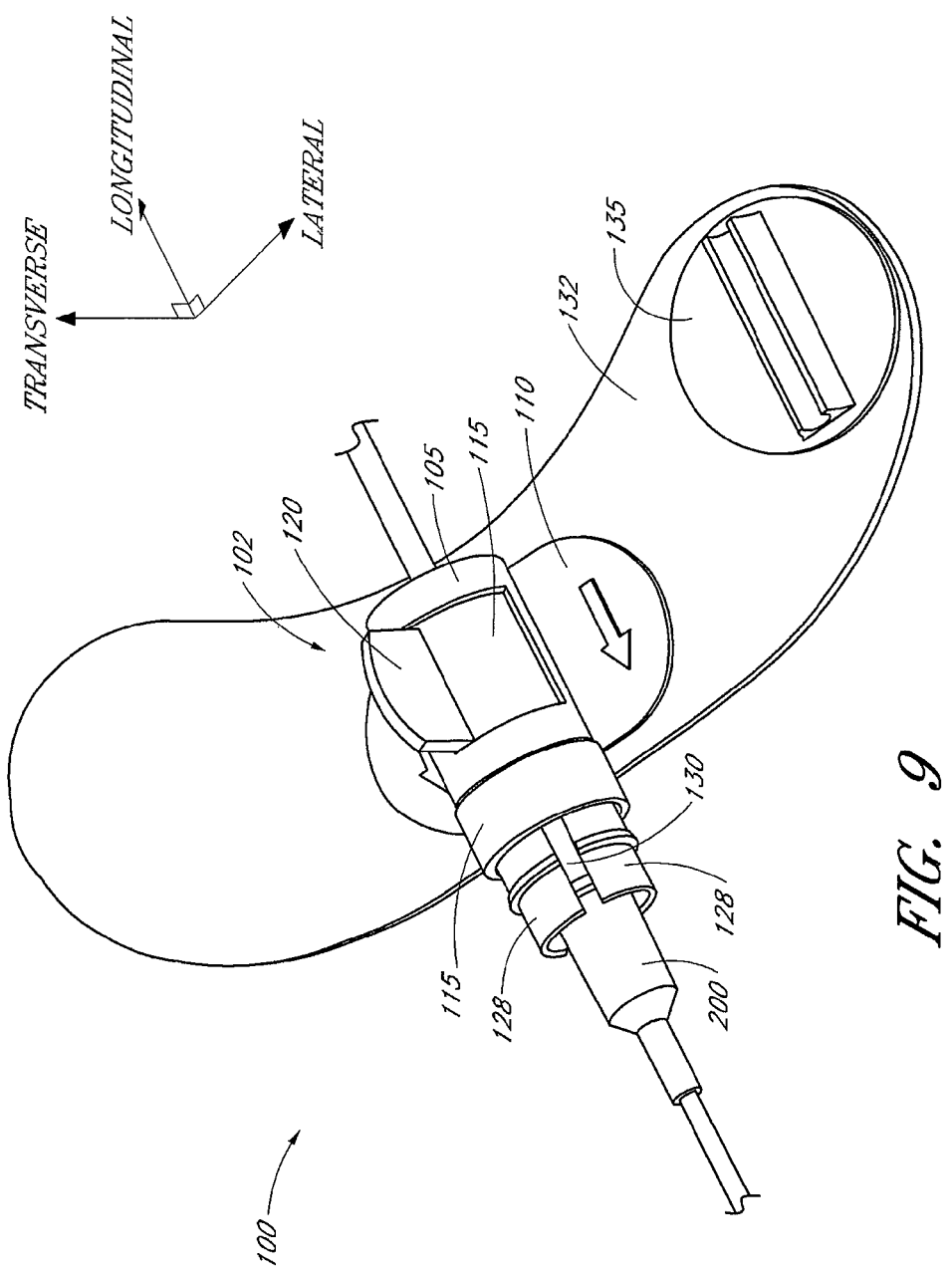
FIG. 9 is a perspective view of the securement device from FIG. 8 in the open condition with the medical article inserted into an end of the securement device.
Figure 10:
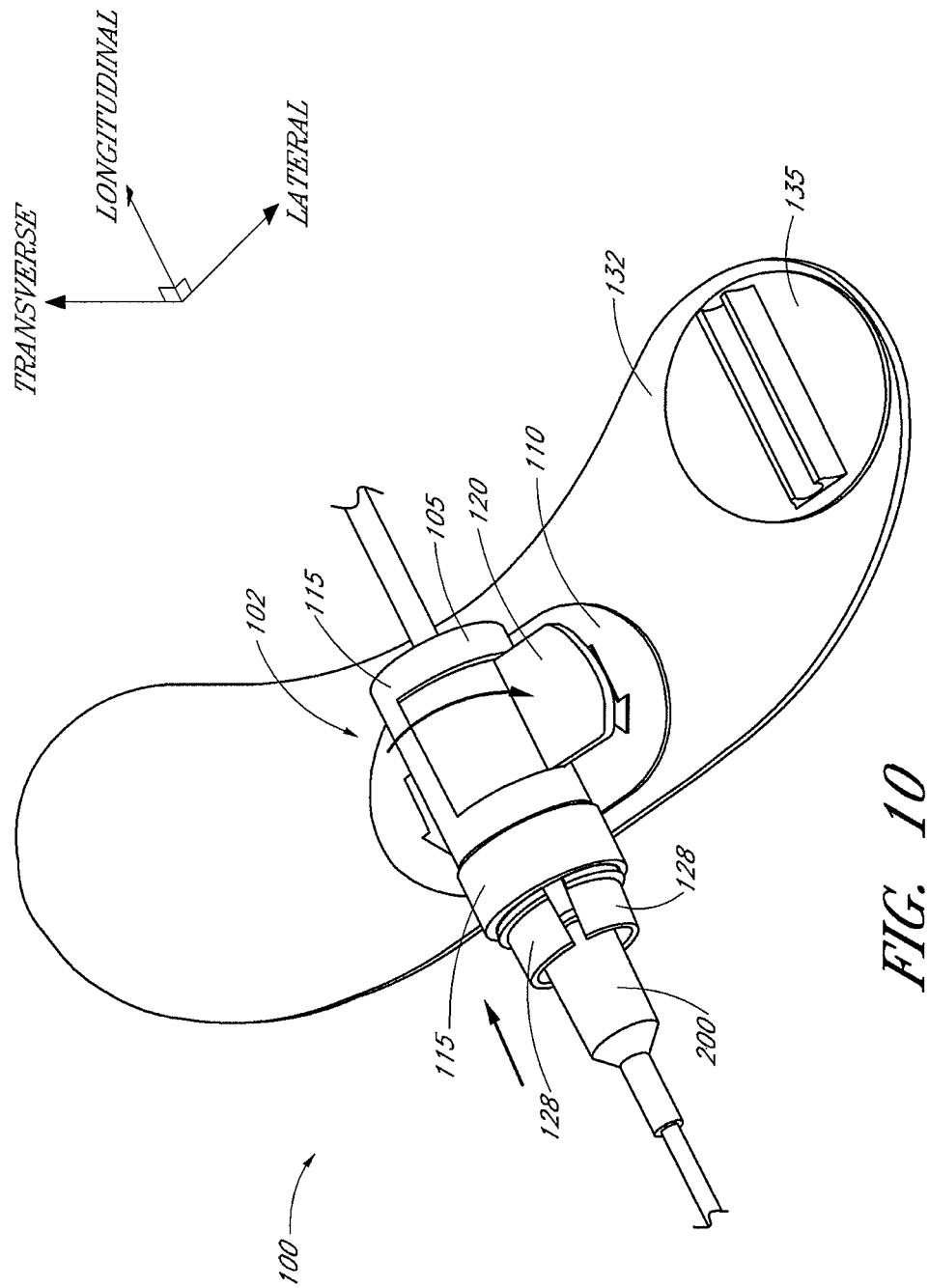
FIG. 10 is a perspective view of the securement device from FIG. 9 in a closed condition with the medical article secured in the securement device.

Positioning the catheter hub 200 in the receptacle defined by the clamp 125 places the catheter in fluid communication with the tubular portion 130 of the base 105 as shown in FIG. 9. The catheter hub 200 may have a tubular shape defining a lumen. Accordingly, positioning the catheter hub 200 in the clamp 125 aligns the lumen of the catheter hub 200 with the lumen of the base 105 forming a flow passage through which fluid may pass between the two lumens. Further, rotating the locking mechanism 115 moves the clamp 125 into the closed position and retains the catheter hub 200 as shown in FIG. 10.

A tube may be in fluid communication with the tubular portion 130 of the base 105 and may extend in the longitudinal direction from the retainer 102. The securement device may further comprise a supplemental securement structure, such as a clip 135. The clip is positioned on the anchor pad 132. The clip 135 may be placed laterally from the retainer 102. The clip 135 may comprise a channel that extends in the longitudinal direction. The clip 135 may be configured to receive a portion of the tube. The tube enters the clip 135 by moving the tube in a transverse direction relative to the clip 135. The clip 135 comprise walls that inhibit lateral movement of the tube.

Figure 11:
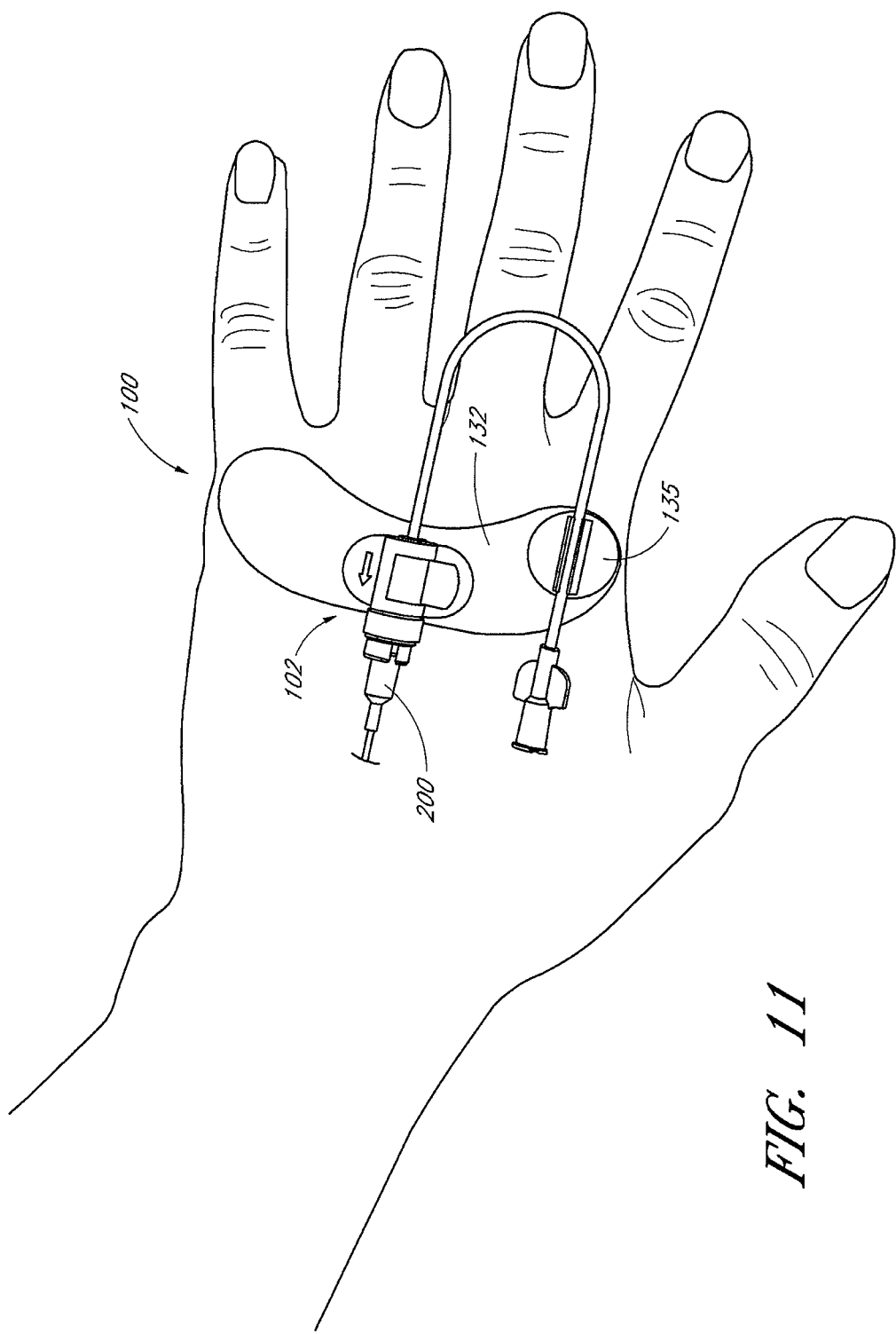
FIG. 11 illustrates a top view of the securement device of FIG. 1 in a closed condition with the medical article secured in the securement device and the anchor pad adhered to a patient.

The securement device 100 may be placed on the skin of a patient to hold a catheter in place on the patient as shown in FIG. 11.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but by a fair reading of the claims that follow.

What is claimed is:

1. A securement device for securing a medical article to a patient, the device comprising:
    an anchor pad having a lower surface, at least a portion of the lower surface being covered by an adhesive; and
    a collet supported by the anchor pad, the collet being movable between an open position and a closed position, the collet exerting a radially and longitudinally inward clamping force on the medical article when in the closed position, the collet decreasing in cross-sectional area and moving in a distal direction relative to the anchor pad as the collet moves from the open to the closed position.

2. The securement device of claim 1 further comprising a locking mechanism forming a tapered sleeve, a first portion of the collet being disposed in the sleeve when in the open position and a second portion of the collet being disposed in the sleeve when in the closed position, the first portion being smaller than the second portion.

3. The securement device of claim 1 further comprising a lumen, the lumen being coaxially disposed within the collet and configured to flow a liquid through the medical article and into the patient.

4. The securement device of claim 1 further comprising an actuator, wherein movement of the actuator moves the collet between the open and closed positions.

5. The securement device of claim 1, wherein the collet generally moves along a longitudinal axis thereof.

6. The securement device of claim 1, wherein the collet comprises a plurality of latching members, the latching members applying the clamping force to the medical article when the collet is in the closed position.

7. A securement device for a medical article having a first lumen extending therethrough, comprising:
    an anchor pad, at least a portion of a lower surface of the anchor pad being covered by an adhesive;
    a base member supported by the anchor pad and forming a second lumen therethrough;
    a member movable in a radially and longitudinally inward direction relative to the base member between an open position and a closed position, the member and base member defining a receptacle for receiving at least a portion of the medical article when in the open position; and
    a lever moving the member from the open position to the closed position so as to secure a received portion of the medical article relative to the base member and form a flow passage between the first and second lumens.

8. The securement device of claim 7, wherein at least a portion of the member is rotatable with respect to the base member.

9. The securement device of claim 8, wherein the lever is configured to rotate the member from the open position to the closed position.

10. The securement device of claim 8, wherein the lever is rotatable about a longitudinal axis.

11. The securement device of claim 7, wherein the member forms a channel having a generally conical shape that decreases in diameter in a longitudinal direction.

12. The securement device of claim 7, wherein the receptacle extends in a longitudinal direction.

13. The securement device of claim 7, wherein the member is configured to inhibit movement of the medical article in a longitudinal direction when in the closed position.

14. The securement device of claim 7, wherein the received portion of the medical article comprises a catheter hub.

15. The securement device of claim 7, wherein the member comprises a locking mechanism.

16. The securement device of claim 7, wherein the member comprises a clamp.

17. The securement device of claim 16, wherein the clamp comprises a collapsing collet.

18. A retainer for a medical article having a first lumen extending therethrough, comprising:
    a base member forming a second lumen therethrough;
    a member movable in a radially and longitudinally inward direction relative to the base member between an open position and a closed position, the member and the base member defining a receptacle for receiving at least a portion of the medical article when in the open position; and
    a lever for moving the member from the open position to the closed position so as to secure a received portion of the medical article relative to the base member.

19. The securement device of claim 18, wherein the member forms at least a portion of a channel, the channel having a generally tapering shape.

20. The securement device of claim 18, wherein the member comprises a clamp.

* * * * *